United States Patent [19]
Donohue

[11] Patent Number: 5,469,048
[45] Date of Patent: Nov. 21, 1995

[54] CATHODIC PROTECTION MEASUREMENT APPARATUS

[75] Inventor: Charles W. Donohue, Farmington, N.M.

[73] Assignee: Meridian Oil Inc., Houston, Tex.

[21] Appl. No.: 258,687

[22] Filed: Jun. 13, 1994

[51] Int. Cl.⁶ .................................................. G01N 27/42
[52] U.S. Cl. .......................... 324/71.1; 324/425; 204/404
[58] Field of Search .................................. 324/425, 71.1, 324/71.2, 700, 713; 204/404, 153.11; 307/95

[56] References Cited

U.S. PATENT DOCUMENTS

| | | | |
|---|---|---|---|
| 2,862,177 | 11/1958 | Titterington . | |
| 3,893,026 | 7/1975 | Glazkov et al. | 324/72 |
| 4,255,241 | 3/1981 | Kroon et al. | 204/147 |
| 4,356,444 | 10/1982 | Saenz, Jr. | 324/559 |
| 4,357,573 | 11/1982 | Huezé | 324/559 |
| 4,437,065 | 3/1984 | Woudstra | 324/425 |
| 4,438,391 | 3/1984 | Rog et al. | 324/71.1 |
| 4,467,274 | 8/1984 | Bushman et al. | 324/71.1 |
| 4,511,844 | 4/1985 | Tietze | 324/425 |
| 4,839,580 | 6/1989 | Moore et al. | 324/700 X |
| 5,144,247 | 9/1992 | Speck | 324/71.1 X |
| 5,216,370 | 6/1993 | Bushman et al. | 324/71.1 X |

OTHER PUBLICATIONS

A. W. Peabody; "Control of Pipeline Corrosion;" National Association of Corrosion Engineers, 2400 West Loop South, Houston, Tex. 77027; p. 37.

Primary Examiner—Kenneth A. Wieder
Assistant Examiner—Diep Do
Attorney, Agent, or Firm—Pravel, Hewitt, Kimball & Krieger

[57] ABSTRACT

A cathodic protection measurement apparatus including a coupon made of similar material as a buried metal pipeline to form an artificial holiday, where the coupon is buried near and electrically connected to the pipeline to receive the same level of cathodic protection current as the pipeline. A test wire is connected to the pipeline and routed to a normally-closed contact switch located at an access point of a test station. The switch is also connected to a coupon wire, which is routed and connected to the coupon to complete the electrical connection. A reference electrode having a measuring surface contacting the soil close to the buried coupon includes an electrode wire provided to the access point. A voltmeter is connected between the switch and the reference electrode wire, and the switch is then opened to electrically isolate the coupon from the pipeline. Thus, the on potential, the instant off potential, the I/R voltage drop free potential and the polarization decay of the coupon is measured, simulating the measurements of the pipeline. An ammeter may be connected to the contacts of the switch to measure the cathodic protection current received by the coupon.

19 Claims, 3 Drawing Sheets

CATHODIC PROTECTION MEASUREMENT APPARATUS

BACKGROUND OF THE INVENTION

1. Field of the Invention

The present invention relates to cathodic protection measurement apparatus for measuring the potential difference between a buried structure receiving cathodic protection and the surrounding soil.

2. Description of the Related Art

Corrosion of a buried metal structure is a destructive attack on the metal, which is generally electrochemical in nature. The mechanism of electrochemical corrosion occurs in two parts: (1) an anodic reaction, in which the metal dissolves in an electrolyte in the form of positively charged ions, and (2) a cathodic reaction, in which positively charged hydrogen ions plate out as atomic hydrogen on the cathodic surface. The electrons released by the anodic reaction flow through the metallic circuit to the cathode, where they neutralize an exactly equivalent number of hydrogen ions. Thousands of microscopic corrosion cells are formed along the surface of the metal structure, where the metal structure serves as an anode and the soil serves as an electrolyte. Thus, the metal dissolves by releasing electrons into the soil to neutralize hydrogen ions.

The metal may be coated with zinc, tin, lead, nickel, copper, chromium, aluminum or various other types of coatings applied using a variety of processes, including galvanizing, sherardizing, metal spraying or metalizing, electrolytic, cold process or hot processes as known to those skilled in the art. An appropriate coating can retard or almost eliminate corrosion over most of the surface of the buried structure. However, small imperfections or scratches in the coating expose the bare metal to the soil. The exposed locations and other discontinuities of the coating are generally referred to as "holidays," which become anodic and begin the corroding process.

Cathodic protection is a technique used to protect buried metal structures from corrosion. A cathodic protection system protects a structure by applying a DC voltage, causing the structure to become cathodic by collecting current. The DC voltage forces current to flow from a purposely established ground connection through the earth and onto the structure to be protected. There are two primary types of cathodic protection systems. The first type uses sacrificial or galvanic anodes, which are made of a metal that is more negative in the galvanic series than the metal to be protected. The galvanic series is a measure of the tendency of a metal to dissolve in water, known as solution pressure, which can be measured by the amount of electrical potential that must be applied to prevent dissolution when the metal is dissolved in one of its salts at standard concentration. When two metals are immersed in an electrolyte, such as soil, that metal which is above the other in the series becomes anodic, suffers corrosion, and protects the other metal by rendering it cathodic.

A second type of cathodic protection is an impressed current system. An impressed current system uses an outside source of DC voltage and current, which is connected with its negative terminal to the buried metal structure to be protected, such as a buried pipeline, and with its positive terminal connected to one or more earth contacting anodes or ground beds of a material having a low rate of dissolution. Current is forced to flow from the ground bed and through the electrolyte to the metal pipeline. Applied voltage and circuit resistances may be adjusted to permit circulation of the required amount of current to attain full protection. Impressed current systems are implemented in several different ways depending upon the available source of power. If commercial AC power source is available, a rectifier is used to convert the AC power to a low voltage DC source. Other means of electric power may be used, such as engines, turbines, or thermal generators, fuel cells, or even batteries when other sources of power are not practical.

Once a cathodic protection system is in place, the level of cathodic protection must be periodically tested to assure proper protection. The potential difference between a buried metal pipeline and the soil is of considerable importance, either in investigating the corrosive conditions or in evaluating the extent of cathodic protection being applied. The potential difference, often referred to as the pipe-to-soil (P/S) potential, is measured while cathodic protection is being applied. The P/S potential is measured by connecting a measuring instrument between the pipeline through direct metal contact and a reference electrode placed in contact with the soil. A series of test points or test stations are provided along the pipeline, where each test point includes a test wire electrically coupled to the pipeline and brought to the surface through a hollow access tube, usually made of plastic or poly-vinyl-chloride (PVC). The electrical connection of the test wire to the pipeline is preferably made by a welded or soldered lead. The reference electrode used for measuring the potential difference is a half-cell having a known voltage level for establishing a voltage reference, where the half-cell is preferably a copper-copper sulfate half-cell known to those skilled in the art.

To measure the level of cathodic protection, the reference electrode is preferably placed on the soil as close to the metal pipeline as possible. It is desired to penetrate the soil down to within about 6 inches of the pipeline, but this is often not convenient or feasible. Usually, the reference electrode is placed directly above the buried metal pipeline on the surface of the ground. In general, the test wire is connected to the negative terminal of a high resistance voltmeter, having its positive terminal connected to the terminal of the reference electrode placed on the ground. In this manner, a galvanic cell or small battery is achieved through connecting two half-cells together, the first half-cell being the natural half cells formed between the pipeline and the soil, and the second half-cell being the reference electrode.

There are several errors that are introduced when taking cathodic protection measurements as described above. The errors are primarily caused by I/R voltage drops while the cathodic protection system is activated and current is flowing. An I/R voltage drop is simply a voltage drop caused by current flow through a resistive element in accordance with Ohm's law. Resistive elements include test lead connections, the soil between the pipeline and the reference electrode, the interface between the pipeline and its coating and other physical elements. Proper practice can reduce I/R voltage drop caused by the test leads to some extent. The I/R voltage drop due to the soil electrolyte can be substantially eliminated by digging a hole and placing the reference electrode within six inches of the pipeline. As described above, however, this is often not practical. Even if all appropriate procedures are practiced, I/R voltage drop may still be substantial if the cathodic protection current is significant. The total I/R voltage drop must be estimated or measured and subtracted out or otherwise accounted for.

The only known way to completely eliminate the I/R voltage drops to is deactivate the cathodic protection system to stop current flow. This, however, also removes the cathodic protection being measured. Nonetheless, if all cathodic protection currents are interrupted simultaneously while monitoring the voltage potential, an initial instantaneous voltage drop is observed, which is approximately equal to the total I/R voltage drop. The new instantaneous voltage level is the true P/S potential indicating the level of cathodic protection, plus the voltage of the reference electrode. This "I/R-free" P/S potential does not last, however, because another voltage shift begins to occur due to depolarization.

Polarization is a desirable effect that occurs at the P/S junction, where ions are reduced to hydrogen as a result of the passage of current directly to or from an electrolyte. Polarization often takes hours or even days to stabilize after cathodic protection is applied. After the cathodic protection potential is removed, depolarization begins causing a decay or decrease in the measured P/S potential. The depolarization occurs more quickly at first, then gradually decreases and stabilizes over time. A minimum negative polarization voltage shift of 100 millivolts (mV) is often specified to indicate adequate cathodic protection. Thus, it is desirable to measure both the I/R free P/S potential and the amount of depolarization.

Temporarily stopping the current flow is difficult, if not impossible, in a galvanic anode system. The conductor between the metal pipeline and each galvanic anode must be readily accessible, and each one of the anodes must be accessed and terminated simultaneously while taking measurements. Often, however, the anodes are buried along with the conductor between each anode and the metal pipeline, so that the conductors are inaccessible. Even if accessible, it would be substantially difficult to locate and simultaneously turn off each anode while taking test measurements. This is usually not practiced.

Temporarily and simultaneously terminating all cathodic current flow in an impressed current system is somewhat easier than for a galvanic anode system. Usually, the power sources are located above ground and are sometimes even designed to be switched off for the purpose of cathodic protection measurements. Of course, all of the power sources must be switched off simultaneously to achieve the most accurate measurements. Impressed current systems are presently in use which use a current interruption procedure, where a particular measurement schedule is defined. During the measurement period, all sources of cathodic protection are synchronously switched on and off periodically. The basis of this interruption method is that I/R voltage drops immediately become zero, permitting I/R free readings before significant depolarization begins. Various duty cycles are possible to achieve fast or slow cycle interruption. For example, a three hour period may be scheduled on a particular day, where each of the power sources remain on for 45 seconds and then are turned off for 15 seconds for each minute during the entire three hour measurement period. This is an example of a slow cycle. In a fast cycle interruption procedure, the rectifiers are shut off for a much shorter period of time, such as 0.1 seconds of each 0.6 seconds. Many various schemes are possible. Thus, a technician aware of the interruption schedule can take the appropriate measurements at the appropriate time.

The current interruption techniques for impressed current systems are rather elaborate and very expensive. Such a system is only feasible if designed initially, and then only if the expense can be justified. Many pipelines and cathodic protection systems exist which do not use these techniques. Also many projects cannot afford them. Further, current interruption schemes are not always convenient, since the technician must be aware of and be available during the scheduled measurement periods. Sophisticated electrical equipment is often required to take the measurements, especially for fast interruption cycles. Therefore, current interruption techniques used in impressed current systems have relatively limited use.

It is desired to provide a means for measuring cathodic protection without I/R voltage drop errors for all types of cathodic protection systems, by accurately measuring the potential difference between a buried structure and the surrounding soil. Further, it is desired to make such measurements conveniently and without excessive cost.

SUMMARY OF THE PRESENT INVENTION

A cathodic protection measurement apparatus according to the present invention includes a coupon made of a similar material as a buried structure being protected, where the coupon is placed near the structure and exposed to the same environment, and where the coupon is electrically connected to the structure to receive the cathodic protection current. The coupon does not have a protective coating, so that it serves as an artificial holiday for the structure. In a typical test station or test point, such as a three-inch test point, a PVC access tube provides a channel for a test wire electrically connected to the structure, which is preferably a buried pipeline. The coupon is preferably mounted through the wall of the access tube about six inches from the pipeline. Since the coupon penetrates and extends into the soil surrounding the pipeline, it is exposed to the same electrolytic environment. A conductor is attached to the coupon, routed to an access point of the test station through the access tube and connected to one contact of a normally-closed contact switch. The other contact of the switch is connected to the test wire, thereby completing a conductive path between the coupon and the buried pipeline. A second tube, called an electrode tube, is preferably placed adjacent to the access tube to provide an electrode channel through the soil to access the soil near the coupon. In this manner, a reference electrode may be lowered and placed in contact with the soil in close proximity to the coupon for making the measurements.

To measure the level of cathodic protection, a technician lowers a reference electrode, such as a copper-copper sulfate half-cell, through the electrode tube to contact the soil near the coupon. An appropriate voltmeter is then connected between the switch and the wire from the reference electrode. Since the coupon serves as an artificial holiday for the metal pipeline, the voltage reading of the voltmeter provides the on potential of the pipeline, virtually eliminating the pipe to surface electrolyte I/R voltage drop through the soil. The cathodic current flowing to the coupon is immediately interrupted from the collection point by opening the switch, and an instant off potential, or I/R free reading, is taken. The switch removes the cathodic protection current from the coupon without removing the cathodic current to the pipeline. Thus, the switch serves to isolate the coupon from the pipeline and cathodic currents while measurements are taken. Polarization decay is measured by monitoring the voltmeter over time while the switch remains open. Current collection can also be measured with an appropriate ammeter coupled between the switch contacts while open.

It is appreciated that a cathodic protection measurement apparatus according to the present invention is relatively inexpensive, simple to implement, and yet provides accurate cathodic protection measurements that can be made at any convenient time.

BRIEF DESCRIPTION OF THE DRAWINGS

A better understanding of the present invention can be obtained when the following detailed description of the preferred embodiment is considered in conjunction with the following drawings, in which.

DETAILED DESCRIPTION OF THE PREFERRED EMBODIMENT

Figure 1:
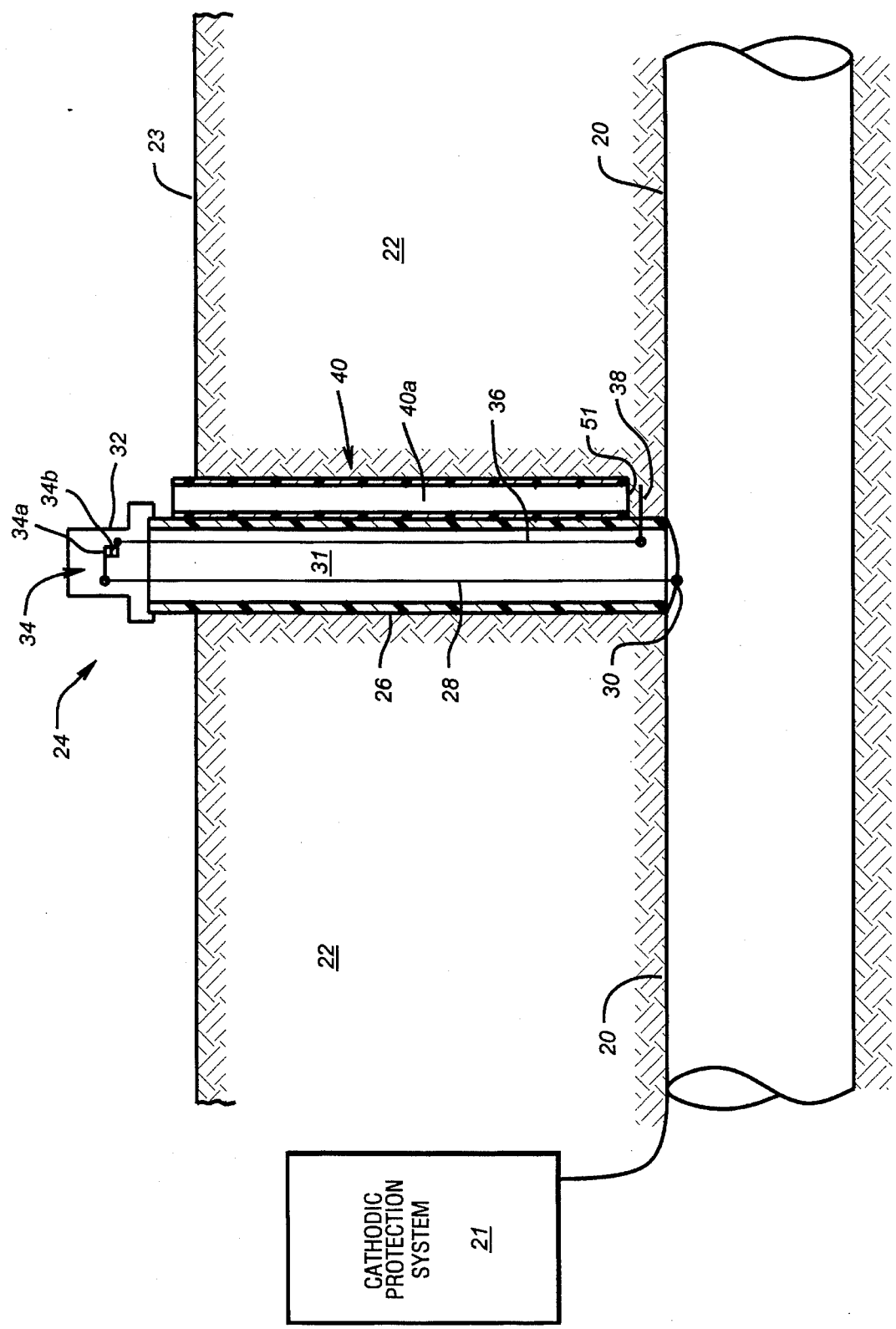
FIG. 1 is a cross-sectional side view of a test station incorporating the cathodic protection measurement apparatus according to the present invention.

Referring now to FIG. 1, a test station 24 is shown illustrating a cathodic protection measurement apparatus according to the present invention. A structure, such as a metal pipeline 20, receives cathodic protection from a cathodic protection system 21, which is preferably either a galvanic or an impressed current system. The present invention, however, is not limited to any particular type of cathodic protection system. The pipeline 20 is buried in the ground or soil 22 at approximately six feet below the surface 23 of the earth. As will be illustrated below, the cathodic protection system 21 providing cathodic protection current to the pipeline 20 need not be interrupted to take the necessary cathodic protection measurements.

The test station 24 preferably includes a three-inch test point comprising a tubular access tube 26, preferably comprising plastic or PVC, which penetrates the soil 22 below the surface 23 to the pipeline 20. The access tube 26 provides a channel 31 for a test wire 28 extending between the surface 23 to the pipeline 20, where one end the test wire 28 is electrically connected to the metal pipeline 20 at an electrical contact point 30. The test wire 28 is preferably made from AWG #10 wire, although any type of conductive wire suitable for cathodic protection systems is contemplated. The electrical connection 30 between the test wire 28 and the pipeline 20 is preferably welded or soldered. A cap access 32 is mounted to the access tube 26 at the surface 23 for accessing the other end of the test wire 28. Of course, other types of test points providing the test wire 28 to the surface 23 for convenient access could be used.

The test wire 28 is preferably attached to one terminal 34a of a normally-closed contact switch 34 located in the cap access 32. The other terminal 34b of the switch 34 is attached to a coupon wire 36, which is routed back down the channel 31 of the access tube 26, and which is electrically connected to a one-quarter inch (¼") round corrosion-monitoring coupon 38. Again, the coupon wire 36 preferably comprises AWG #10 wire, similar to the test wire 28, and is preferably insulated to prevent shorting to the test wire 28. The coupon 38 is buried in the soil 22 surrounding the pipeline 20. For convenience, the coupon 38 is preferably mounted through the side wall of the access tube 26, so that it extends from the channel 31 into the soil 22, where it penetrates the soil approximately 1 inch or more. Also, the coupon 38 is preferably located approximately six inches from the pipeline 20, to place the coupon 38 in about the same electrolytic environment as the pipeline 20. Although it is not absolutely necessary, it is considered desirable to place the coupon 38 relatively close to the pipeline 20 to achieve the most accurate measurements.

The coupon 38 is preferably made of the same type of metal as the pipeline 20 for the most accurate results. However, it has been determined that the coupon 30 need only be made of a similar metal material as the pipeline 20, and thus need not be the exact material to achieve accurate measurements. The coupon 30 is preferably not coated with the same protective coating typically applied to the surface of the pipeline 20. Due to the electrical conduction through the test wire 28, the closed switch 34 and the coupon wire 36, the coupon 38 is electrically connected to the pipeline 20. In this manner, the coupon 38 forms an artificial holiday, which is exposed to the same environment and which receives about the same level of cathodic protection currents as the pipeline 20.

Another tube made of plastic or PVC, referred to as the electrode tube 40, is mounted adjacent to the access tube 26 and extends from the surface 23 through the soil 22 to a location 51 in the soil 22 near the coupon 38. The electrode tube 40 is preferably a 1¼" round hollow access tube, which forms a channel 40a extending from the surface 23 down to the location 51 in the soil 22, which is preferably approximately one inch above the coupon 38. The channel 40a has a sufficient inner diameter to allow a reference electrode 50 (FIG. 2) to be lowered to the coupon 38.

Figure 2:
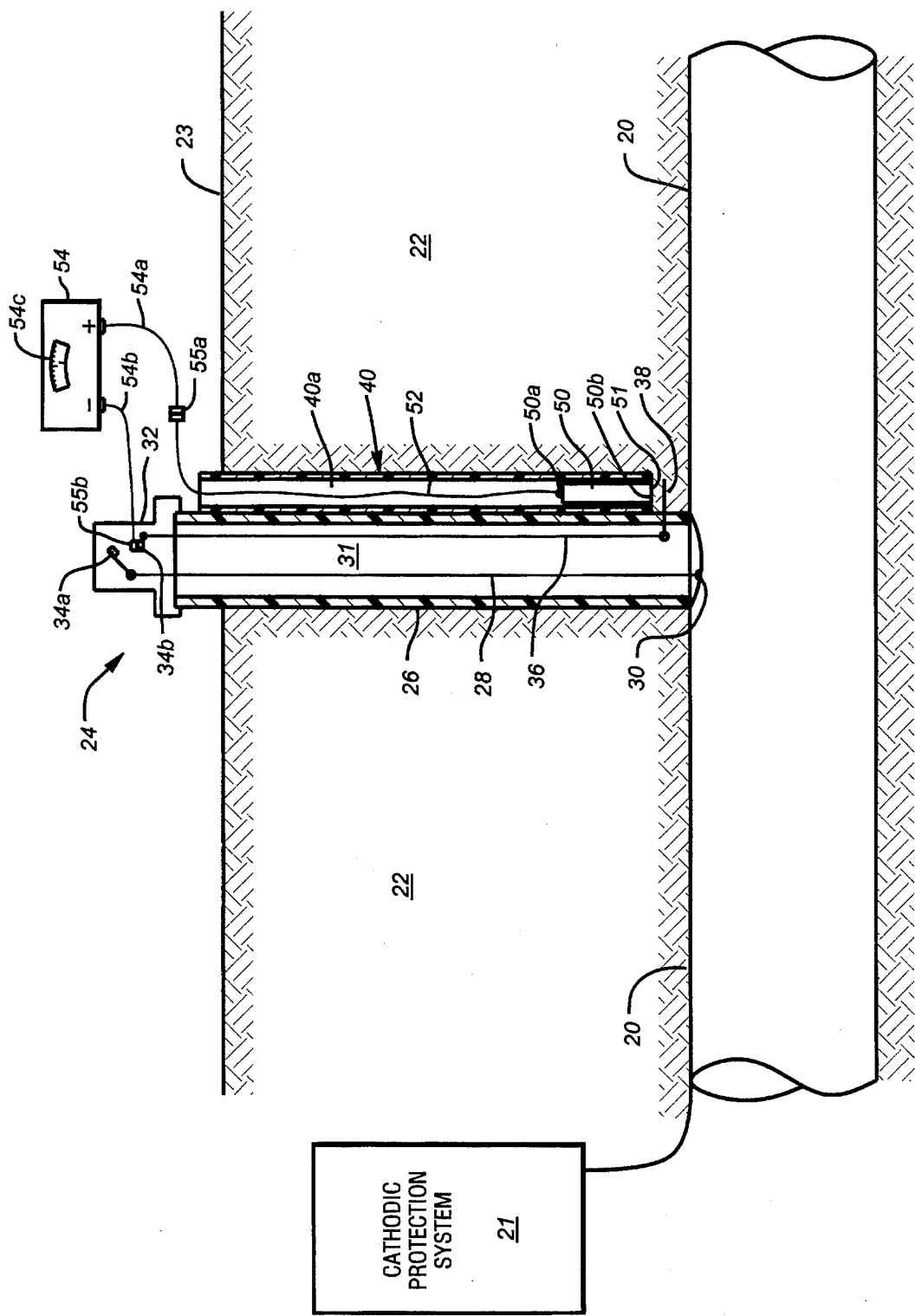
FIG. 2 is a partial cross-sectional side view illustrating cathodic protection measurements using the cathodic protection measurement apparatus of FIG. 1.

Referring now to FIG. 2, a partial cross-sectional side view is shown on the cathodic protection measurement apparatus according to the present invention being used to make cathodic protection measurements. As shown, the reference electrode 50 has been lowered within the electrode tube 40 to the location 51. The reference electrode 50 preferably includes a measuring surface 50b, which contacts the soil 22 at the location 51. The location 51 is sufficiently close to the coupon 38 to substantially remove any potential drop across the soil 22 between the reference electrode 50 and the coupon 38. The reference electrode 50 is preferably a copper-copper sulfate half-cell electrode as known to those having ordinary skill in the art, although other standard reference cells may be used. An electrode conductive wire 52 connected to a terminal 50a of the reference electrode 50 is brought to the surface 23 through the channel 40a and used for measurement. The reference electrode 50 has a known electrode potential, which is reasonably constant under a wide range of soil conditions.

As known to those skilled in the art of taking cathodic protection measurements, the reference electrode 50 is used in conjunction with natural electrodes created between the pipeline 20 and the soil 22 to form a galvanic cell or small battery. The total combined cell voltage is measured to determine the P/S potential. However, any errors caused by I/R voltage drops must be determined and subtracted to find the true P/S potential. In an alternative embodiment, the reference electrode is permanently buried in the soil 22 substantially near the coupon 38. In this case, the electrode tube 40, or some other similar means, is provided to bring the electrode wire 52 to the cap access 32.

A conductive lead 54a is connected between the positive terminal of a suitable high resistance voltmeter 54 to the electrode wire 52 through an electrical contact 55a. Likewise, a conductive lead 54b is electrically connected between the negative terminal of the voltmeter 54 and the terminal 34b of the switch 34 through an electrical contact 55b. The voltmeter 54 preferably includes a scale 54c for providing a visual indication of the measured potentials. The voltmeter 54 also preferably includes means for measuring and indicating or storing voltage values over time, such as an instrument for generating strip charts similar to that shown in FIG. 3.

Ignoring the potential of the reference electrode 50, while the switch 34 is closed and the cathodic protection system 21 is operating, the scale 54c of the voltmeter 54 reflects the "on" potential between the coupon 38 and the soil 22, including all I/R voltage drops in the galvanic cell system. Then, the switch 34 is pressed to open circuit the contacts 34a and 34b to remove the cathodic protection currents from the coupon 38. In this manner, an isolated galvanic cell is created between the reference electrode 50 and the coupon 38 to soil 22. When the switch 34 is opened, the cathodic protection to the coupon 38 is instantaneously interrupted to achieve an "instant-off" potential of the coupon 38, immediately removing substantially all I/R voltage drops in the isolated galvanic cell. This measurement is substantially equivalent to an instant off potential of the pipeline 20 after all of the cathodic protection currents are removed by simultaneously turning off all sources of the cathodic protection system 21. Then, the potential measured by the voltmeter 54 is monitored over a period of time to measure the polarization decay after the instantaneous I/R voltage drop has been removed. The polarization decay of the coupon 38 is substantially equivalent to the polarization decay of the pipeline 20. It is then determined whether a polarization decay of at least one hundred millivolts (100 mV) is achieved.

Figure 3:
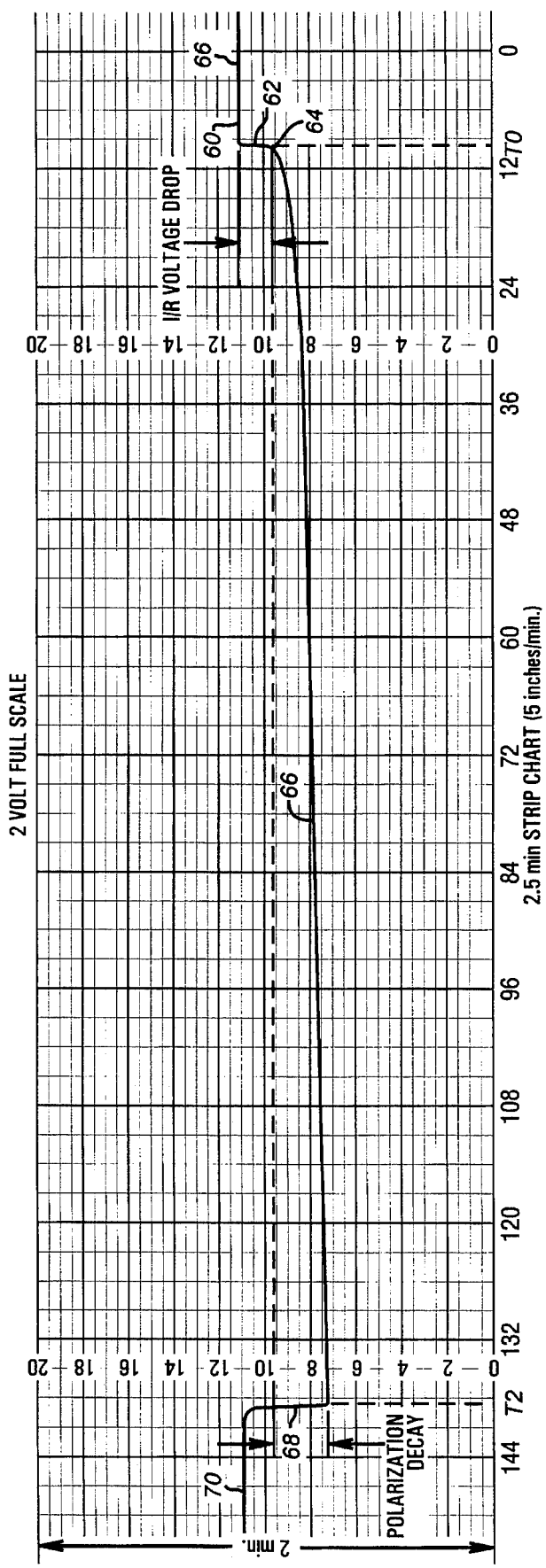
FIG. 3 is a strip chart graph illustrating the measurement taken with the cathodic protection measurement apparatus shown in FIG. 2.

Referring now to FIG. 3, a strip chart is shown of the cathodic protection measurements made using the cathodic protection measurement apparatus shown in FIG. 2. The strip chart in FIG. 3 is read from right to left, where voltage is provided on a 2 volt scale along the vertical axis and elapsed time in seconds is shown from right to left along the horizontal axis. A curve 66 plots the voltage measured by the voltmeter 54. Between zero seconds and a time T0, a plateau 60 shows the on potential measured at the coupon 38, which is approximately 1123 millivolts (mV). It is noted that the on potential at the surface 23 is 1140 mV, which was measured by placing the reference electrode 50 on the surface 23. In this manner, approximately 17 mV of I/R voltage drop error due to electrolytic I/R drop through the soil 22 is immediately removed by placing the reference electrode 50 in the channel 40a of the electrode tube 40 close to the coupon 38.

At a time T0, after approximately 10 seconds, the switch 34 is opened and an instantaneous voltage drop 62 occurs. The switch 34 removes current from the coupon 38, so that the voltage drop 62 represents substantially all of the I/R voltage drop from the initial measurement of 1123 mV at 60. The instant off potential is 950 mV measured at the coupon 38 by the voltmeter 54. The 950 mV measurement is the sum of the true P/S potential representing the cathodic protection received by the pipeline 20 from the cathodic protection system 21 and the voltage of the reference electrode 50.

After dropping to 950 millivolts, the voltage potential begins to decay because of depolarization. The polarization decay begins at a point 64 along the curve 66 almost immediately after the switch 34 was opened. The voltmeter 54 is monitored over time to determine the extent of the polarization decay. An elapsed time of approximately 2 minutes is shown while polarization decay occurs. After about 130 seconds from time T0 at a time T2, the voltage potential has decayed to approximately 750 millivolts, illustrating a polarization decay of approximately 225 mV. Since only 100 mV of polarization decay is desired, the polarization shown in FIG. 3 is more than adequate. At time T2, the switch 34 is again closed so that the voltage immediately rises, shown at 68, to the original on potential of 1123 mV, shown at 70.

The cathodic protection current received by the pipeline 20 from the cathodic protection system may also be measured. After removing the voltmeter 54 and closing the contacts 34a, 34b of the switch 34, an ammeter (not shown) is connected between the contacts 34a, 34b while the switch 34 is closed. The switch 34 should remain closed long enough for the polarization to stabilize before taking measurements. Alternatively, the current measurement may be performed first before the potentials and polarization values are measured. The switch 34 is opened after the ammeter is connected, so that cathodic current to the coupon 38 is not interrupted, but flows through the ammeter. A current of 550 milliamps (ma) is measured on the ammeter illustrating the amount of cathodic protection current flowing to the coupon 38. The switch 34 is then closed and the ammeter removed.

It can now be appreciated that a cathodic protection test point according to the present invention provides an inexpensive, accurate and convenient measurement of cathodic protection received by a pipeline or other buried structure, without interrupting the cathodic protection to the structure. A coupon forming an artificial holiday is provided along the test station tube near the structure. A coupon wire and a normally-closed switch are electrically connected between the coupon and the test wire, so that the coupon receives cathodic current. An electrode tube is provided to allow a reference electrode to be lowered to a location near the coupon. The on potential is measured by a voltmeter, and the instant off potential is then measured by opening the switch. Polarization decay is then measured over time. An ammeter is used to measure collection current, if desired.

The foregoing disclosure and description of the invention are illustrative and explanatory thereof, and various changes in the size, shape, materials, components, circuit elements, wiring connections and contacts, as well as in the details of the illustrated circuitry and construction and method of operation may be made without departing from the spirit of the invention.

I claim:

1. A cathodic protection measurement apparatus for measuring the level of cathodic protection provided from a cathodic protection system to a metal structure buried in the soil, the measurements taken at an access point of a test station, the cathodic protection measurement apparatus comprising:

an electrically conductive test wire having a first end electrically connected to the metal structure and a second end provided to the access point;

a normally-closed switch located at the access point, said switch having a first contact and a second contact, wherein said first contact is electrically connected to said second end of said test wire;

a metal coupon buried in the soil surrounding the metal structure;

an electrically conductive coupon wire having a first end electrically coupled to said second contact of said switch and a second end electrically connected to said coupon;

a reference electrode having a measuring surface and a terminal, wherein said measuring surface contacts the soil at a measuring location substantially near said coupon;

an electrically conductive electrode wire having a first end coupled to said reference electrode terminal and a second end provided to the access point; and an access tube provided between the surface of the soil and the buried metal structure providing an access channel;

wherein said cathodic protection current is provided from the cathodic protection system to said coupon while said switch is closed, and wherein said cathodic protection current provided to said coupon is interrupted when said switch is opened.

2. The cathodic protection measurement apparatus of claim 1, wherein said coupon is mounted through the wall of said access tube and extends into the soil surrounding the metal structure.

3. The cathodic protection measurement apparatus of claim 1, wherein said test wire is provided in said access channel.

4. The cathodic protection measurement apparatus of claim 1, wherein said coupon wire is provided in said access channel.

5. The cathodic protection measurement apparatus of claim 1, wherein said reference electrode comprises a copper-copper sulfate half-cell.

6. The cathodic protection measurement apparatus of claim 1, wherein said coupon is made of a similar metal material as the metal structure.

7. The cathodic protection measurement apparatus of claim 1, wherein said coupon is located approximately six inches from the metal structure.

8. The cathodic protection measurement apparatus of claim 1, wherein said measuring location is sufficiently close to said coupon to substantially remove any potential drop across the soil between said coupon and said reference electrode measuring surface.

9. The cathodic protection measurement apparatus of claim 1, wherein said measuring location is approximately one inch from said coupon.

10. The cathodic protection measurement apparatus of claim 1, wherein the metal surface is covered with a protective coating, and wherein said coupon is bare metal and not covered with said protective coating.

11. A cathodic protection measurement apparatus for measuring the level of cathodic protection provided from a cathodic protection system to a metal structure buried in the soil, the measurements taken at an access point of a test station, the cathodic protection measurement apparatus comprising:

an electrically conductive test wire having a first end electrically connected to the metal structure and a second end provided to the access point;

a normally-closed switch located at the access point, said switch having a first contact and a second contact, wherein said first contact is electrically connected to said second end of said test wire;

a metal coupon buried in the soil surrounding the metal structure;

an electrically conductive coupon wire having a first end electrically coupled to said second contact of said switch and a second end electrically connected to said coupon;

a reference electrode having a measuring surface and a terminal, wherein said measuring surface contacts the soil at a measuring location substantially near said coupon;

an electrically conductive electrode wire having a first end coupled to said reference electrode terminal and a second end provided to the access point; and an electrode tube providing an electrode channel between the access point and said measuring location, said reference electrode having been lowered through said electrode channel so that said reference electrode measuring surface is in contact with the soil at said measuring location;

wherein said cathodic protection current is provided from the cathodic protection system to said coupon while said switch is closed, and wherein said cathodic protection current provided to said coupon is interrupted when said switch is opened.

12. The cathodic protection measurement apparatus of claim 11, further comprising:

an access tube provided between the surface of the soil and the buried metal structure providing an access channel.

13. The cathodic protection measurement apparatus of claim 12, wherein said coupon is mounted through the wall of said access tube and extends into the soil surrounding the metal structure, and wherein said electrode tube is mounted adjacent to said access tube.

14. The cathodic protection measurement apparatus of claim 11, wherein said reference electrode comprises a copper-copper sulfate half-cell.

15. The cathodic protection measurement apparatus of claim 6, wherein said coupon is made of a similar metal material as the metal structure.

16. The cathodic protection measurement apparatus of claim 6, wherein said coupon is located approximately six inches from the metal structure.

17. The cathodic protection measurement apparatus of claim 6, wherein said measuring location is sufficiently close to said coupon to substantially remove any potentially drop across the soil between said coupon and said reference electrode measuring surface.

18. The cathodic protection measurement apparatus of claim 11, wherein said measuring location is approximately one inch from said coupon.

19. The cathodic protection measurement apparatus of claim 11, wherein the metal surface is covered with a protective coating, and wherein said coupon is bare metal and not covered with said protective coating.

\* \* \* \* \*